United States Patent [19]

Pleil et al.

[11] Patent Number: 5,447,556
[45] Date of Patent: Sep. 5, 1995

[54] SAMPLE INJECTION APPARATUS AND METHOD

[75] Inventors: Joachim D. Pleil, Durham; Michael L. Stroupe, Denver, both of N.C.

[73] Assignees: Graseby-Anderson, Inc., Smyrna, Ga.; United States of America, Washington, D.C.

[21] Appl. No.: 206,467

[22] Filed: Mar. 4, 1994

[51] Int. Cl.$^6$ .............................. B01D 15/08
[52] U.S. Cl. ........................... 95/87; 95/89; 96/102; 96/105; 96/106
[58] Field of Search ............... 95/82, 87, 89; 96/101–106

[56] References Cited

U.S. PATENT DOCUMENTS

| | | | |
|---|---|---|---|
| 3,309,504 | 3/1967 | Rosso et al. | 96/104 X |
| 3,357,233 | 12/1967 | Roof | 96/106 X |
| 3,417,779 | 12/1968 | Golay | 96/106 X |
| 3,486,298 | 12/1969 | Huebner | 95/87 |
| 3,712,028 | 1/1973 | Deans | 95/82 |
| 4,394,263 | 7/1983 | Dosch et al. | 96/104 X |
| 4,442,217 | 4/1984 | Deans | 95/87 X |
| 4,470,832 | 9/1985 | Sugawara et al. | 55/197 |
| 4,521,225 | 6/1985 | Jenkins et al. | 95/82 X |
| 4,600,559 | 7/1986 | Hiatt | 422/89 |
| 4,617,032 | 10/1986 | Wells | 95/89 |
| 4,814,089 | 3/1989 | Kumar | 95/82 X |
| 4,970,905 | 11/1990 | McClennen et al. | 73/864.34 |
| 4,976,750 | 12/1990 | Munari | 95/82 X |
| 5,108,466 | 4/1992 | Klein et al. | 95/82 X |
| 5,166,076 | 11/1992 | Muller et al. | 436/161 |
| 5,205,845 | 4/1993 | Sacks et al. | 96/105 X |
| 5,250,093 | 10/1993 | Jiang et al. | 95/87 X |

OTHER PUBLICATIONS

Arnold, McClennen and Meuzelaar, Vapor Sampling Device for Direct Short Column Gas Chromatography/Mass Spectrometry Analyses of Atmospheric Vapors, Anal. Chem 63: 299–304 (1991).

Pleil, Demonstration of a Valveless Injection System for Whole Air Analysis of Polar VOCs, in Measurement of Toxic and Related Air Pollutants, 1991 Proceeding.

Rivers, Pleil and Wiener, Detection and Characterization of Volatile Organic Compounds Produced by Indoor Air Bacteria, J. Exp. Analysis & Environ. Epidem. (S1):177–188 (1992).

Abstract-Pleil, Development and Testing of a Gas Chromatograph Inlet System for Determination of High Concentrations of Gas Phase Volatile Organic Compounds in Waste Headspace Samples, Pittsburgh Conference, Mar. 8–12, 1993.

Snyder and Harden, Portable Hand–Held Gas Chromatography/Ion Mobility Spectrometry Device, Anal. Chem 65: 299–306 (1993).

Ragunathan, Krock and Wilkins, Multidimensional Gas Chromatography with Parallel Cryogenic Traps, Anal. Chem. 65: 1012–1016 (1993).

*Primary Examiner*—Robert Spitzer
*Attorney, Agent, or Firm*—Olive & Olive

[57] ABSTRACT

An apparatus for sample concentration for gas chromatography and mass spectrometry for analysis for volatile organic compounds, including a hollow differential pressure switch to switch sample flow non-mechanically, and so that the gas chromatograph and apparatus may be used with different sample levels of volatile organic compounds by changing the timing and temperature parameters by changing the flow non-mechanically. The differential pressure switch preferably has a central helium port, a sample flow port, a sweep flow port, a vent end, and an assist/column flow end; an expansion volume chamber having an inlet tube, which is inserted through the assist/column flow end and extends to halfway between the helium port and sample port, a coiled piece of tubing, and an outlet tube; a primary collection trap coiled about a rod having an entry port for a cryogenic substance, an inlet end, a heater at the inlet end, and an outlet, wherein the expansion volume chamber outlet tube connects to the primary collection trap inlet end; and an assist/column interface having an inlet end connected to the outlet of the primary collection trap, an arm connected to a mass flow controller valve and vacuum system; and an outlet end connected to the analytical column. The method of the invention utilizes this apparatus to concentrate a sample suspected of containing VOC's, by adjusting the temperature, flow rates, and whether particular gas flows are turned on or off.

16 Claims, 9 Drawing Sheets

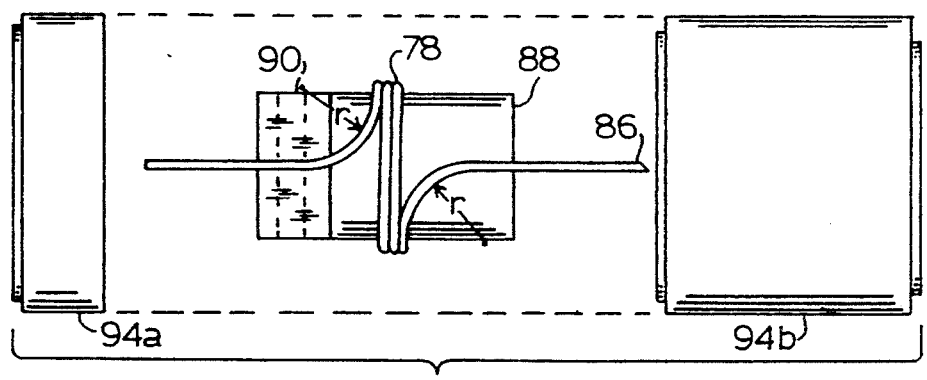
FIG. 3A
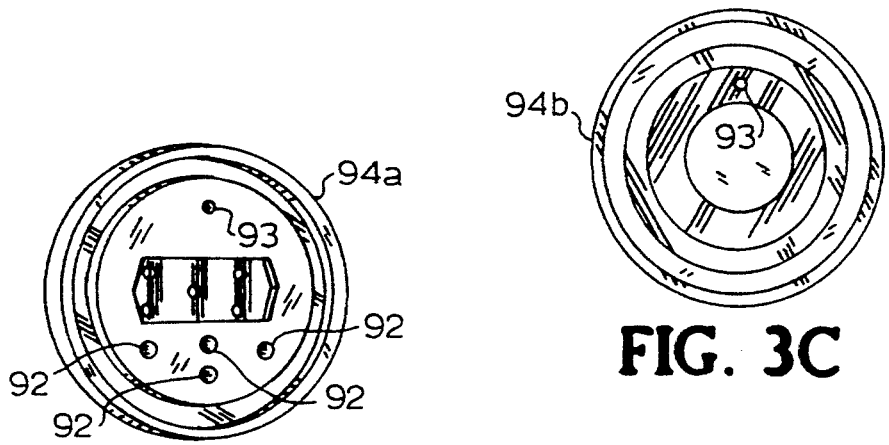
FIG. 3B
FIG. 3C
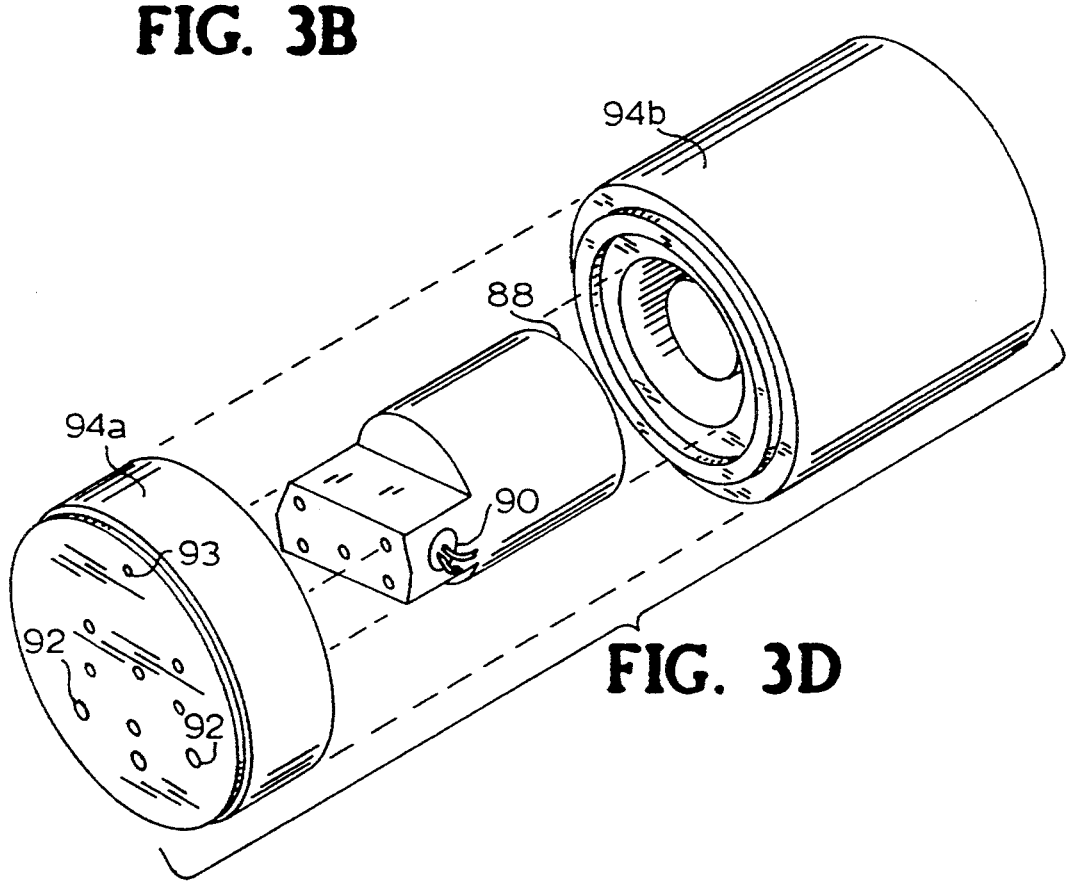
FIG. 3D

SAMPLE INJECTION APPARATUS AND METHOD

STATEMENT AS TO RIGHTS IN INVENTION

This invention was made with Government support and the Government has certain rights in the invention.

BACKGROUND OF THE INVENTION

1. Field of the Invention

This invention relates to systems for performing gas chromatography and mass spectrometry on environmental samples, and in particular, pertains to an apparatus and method for sample injection for analysis of air samples for volatile organic compounds.

2. Description of the Related Art

Many volatile organic compounds (VOCs) are considered to be pollutants and a danger to health even when they are at such low levels in an indoor or outdoor environment that they are only detectable by sophisticated gas chromatography (GC) and mass spectrometry (MS). The sources of undesirable VOCs include such diverse sources as microbial emissions from decay or other biological processes, chemical spills, chemical release from synthetic products, and airborne emissions from industrial processes. VOCs include a wide variety of chemical compounds such as sulfur-containing compounds, aldehydes, alcohols, ketones, chlorinated hydrocarbons, aromatic hydrocarbons, amines, and terpenes.

The very low levels at which many VOCs are toxic or otherwise harmful, in comparison with the higher levels of other compounds present in an average gas sample, means that gas analysis techniques must be very sensitive to the VOCs being analyzed in the presence of higher levels of these other compounds. Techniques such as differential temperature treatment, cryogenic trapping, and use of solid sorbents, or combinations thereof, have been developed in an attempt to remove compounds not being measured and selectively enrich for the VOCs being measured.

It is therefore an object of this invention to provide a method and apparatus which allows detection and measurement of very low levels of VOCs even in samples containing water vapor and/or other components at relatively high levels. The invention thus allows determination of VOCs which may be hazardous to health and the quality of life.

Other objects and advantages will be more fully apparent from the following disclosure and appended claims.

SUMMARY OF THE INVENTION

The invention herein provides an apparatus, for connection to an analytical column of a gas chromatograph for analyzing samples for volatile organic compounds, comprising a hollow differential pressure switch so that sample flow may be switched without mechanical means, and so that the gas chromatograph and apparatus may be used with samples having anywhere from very high to very low levels of volatile organic compounds by merely changing the timing and temperature parameters in the computer control program for the gas chromatographic analysis, and simply changing the flow non-mechanically, without changing anything mechanically.

The apparatus of the invention in its preferred embodiment comprises a hollow differential pressure switch, having a central helium port, a sample flow port on a first side of said helium port, a sweep flow port on a second side of said helium port, a vent end, and an assist/column flow end; an expansion volume chamber having an inlet tube, which is inserted through said assist/column flow end and extends to halfway between said helium port and said sample port, a piece of tubing having a plurality of coils, and an outlet tube; a primary collection (cryogenic) trap comprising a piece of tubing coiled about a rod, said rod having an entry port for a cryogenic substance, an inlet end, a heater at said inlet end, and an outlet, wherein said expansion volume chamber outlet tube connects to the primary collection trap inlet end; and an assist/column interface having an inlet end connected to the outlet of the primary cryogenic trap, an arm connected to a mass flow controller valve and vacuum system; and an outlet end connected to the analytical column. Each pathway that the sample or other gases travel in the apparatus is treated so that the interior surface is inert, such as being coated with fused silica or other surface deactivation process producing an inert surface.

The method of the invention utilizes this apparatus to concentrate a sample suspected of containing VOC's, by adjusting the temperature, flow rates, and whether particular gas flows are turned on or off.

Other aspects and features of the invention will be more fully apparent from the following disclosure and appended claims.

BRIEF DESCRIPTION OF THE DRAWINGS

FIG. 3A is an exploded elevation view of an enclosure and a primary collection trap according to the invention.

FIG. 3B is a perspective view of the inside of an enclosure for a first end of the primary collection trap of FIG. 3A.

FIG. 3C is an elevation view of the inside of an enclosure for a second end of the primary collection trap of FIG. 3A.

FIG. 3D is an exploded perspective view of a primary collection trap enclosure of the invention.

DETAILED DESCRIPTION OF THE INVENTION AND PREFERRED EMBODIMENTS THEREOF

The present invention provides an apparatus and method for processing of samples so that the sample is actually introduced into a GC/MS without encountering any surface in the apparatus other than an inert surface which has been treated with a surface deactivation process, preferably a coating with fused silica, a deactivated fused silica surface, or a specially coated fused silica surface, or with other surface deactivation processes which produce an inert surface such as electro-polishing, or other glass-vapor deposition processes. As used herein, the term "inert" means that the material forming the surface, coating or treatment has no surface chemical activity with organic compounds, no absorption of organic compounds by the material and no re-emanation by the material of organic compounds.

In the preferred embodiment, a fused silica coating is applied to the interior of tubing and other structures with any procedure known in the art. For example, Restek Corporation (Bellefonte, Pa.) utilizes a proprietary process in which high temperatures and pressures are used when applying the coating. When two pieces of coated tubing are joined together, a SWAGELOK TM tube fitting (Swagelok Co., Solon, Ohio) which has also been interiorly coated with fused silica is used to join the two pieces of tubing. Coated fittings and tubing are available from Restek Corporation.

The apparatus of the invention allows VOCs to be measured at the very low levels which are often present in ambient air, in the range of, for example, 0.2 ppbv (parts per billion volume), as well as at the higher levels which may be encountered in industrial, chemical or waste sites, up to saturation vapor pressures, and all levels in between these extremes. This diversity of measurements may be made with only changes in timing sequence and temperature set points in the apparatus and method, and without hardware changes to the apparatus of the invention.

Figure 8:
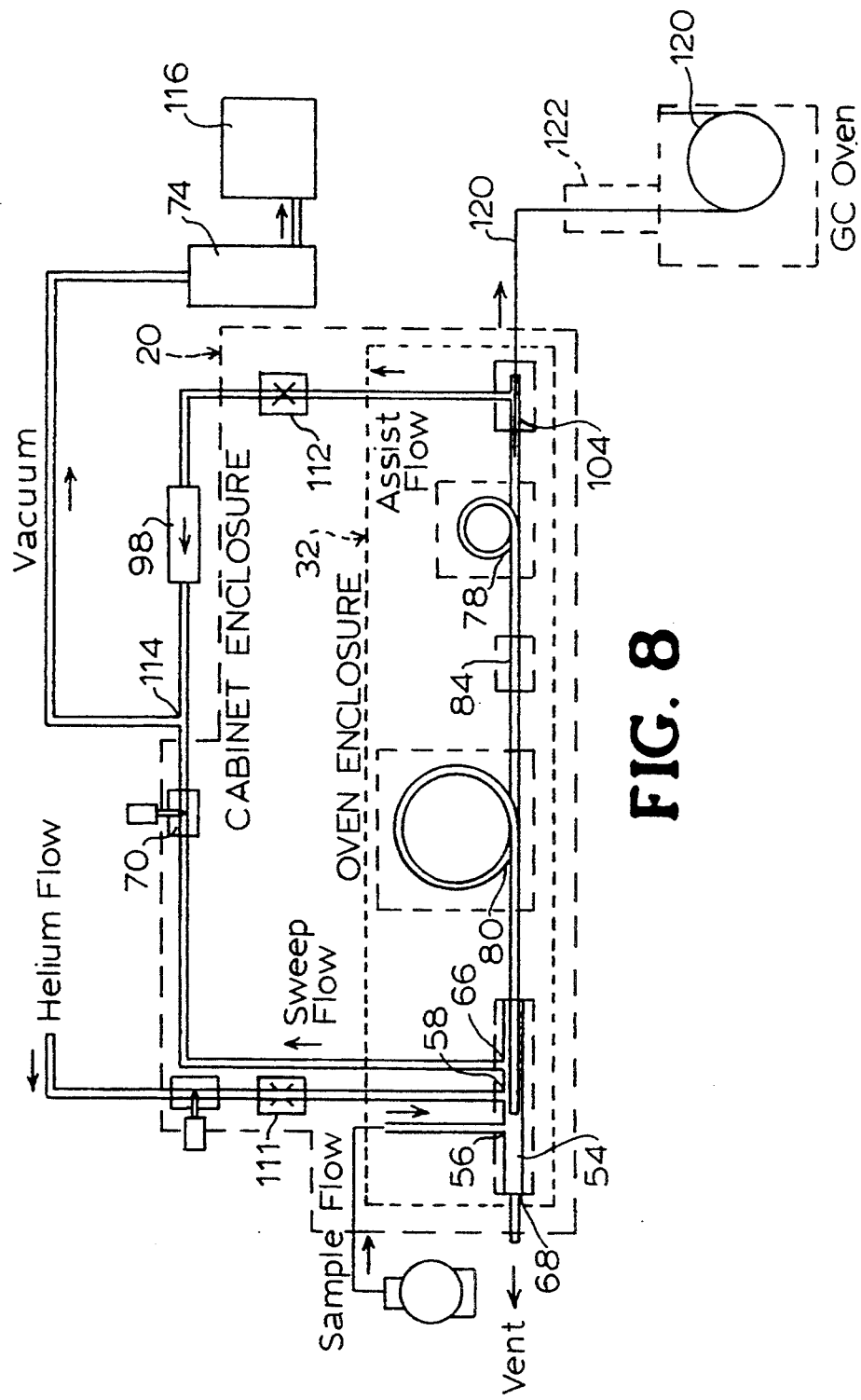
FIG. 8 is a schematic diagram of the apparatus of the invention.

An overall schematic view of the major components of the injection apparatus of the invention is shown in FIG. 8. As discussed in more detail below, the apparatus of the invention comprises four system subassemblies: a differential pressure switch, a primary collection trap and expansion volume chamber, an assist flow, a sample assist/column interface, an external secondary cryogenic focusing assembly, a vacuum source and ballast, and valving and pressure and flow regulation with associated plumbing.

Structure of the Apparatus of the Invention

Figure 4:
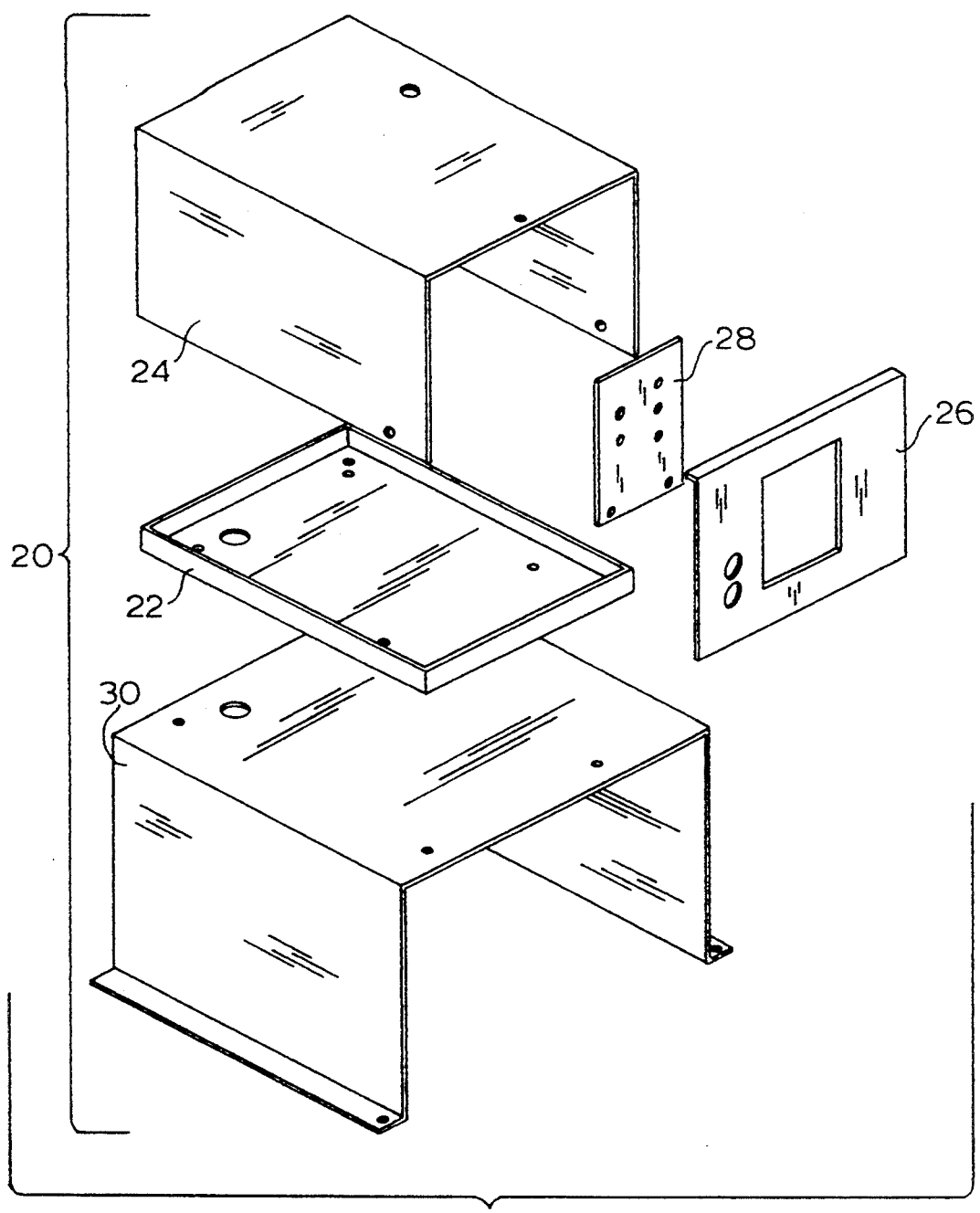
FIG. 4 is an exploded perspective view of a cabinet enclosure which may be used with the invention.

Cabinet enclosure 20 for the invention shown in FIG. 4 and by the outer dotted lines in FIG. 8 is preferably made of aluminum to minimize cost-effectiveness, but other materials may be used without adversely affecting the invention. Cabinet enclosure 20 consists of a base 22, a three sided cover 24, a rear panel 26, and a rear sub-panel 28. Cabinet enclosure 20 is mounted on top of an elevation bracket 30 that positions the injection system over the external refocusing unit for example, a cryofocus unit Model 354A manufactured by Graseby Nutech (Graseby Anderson, Inc., Durham, N.C.) may be used. This unit may be incorporated into cabinet enclosure 20 eliminating the requirement for a bracket. Cabinet enclosure 20 is typically mounted directly to the top of a gas chromatograph.

Figure 5:
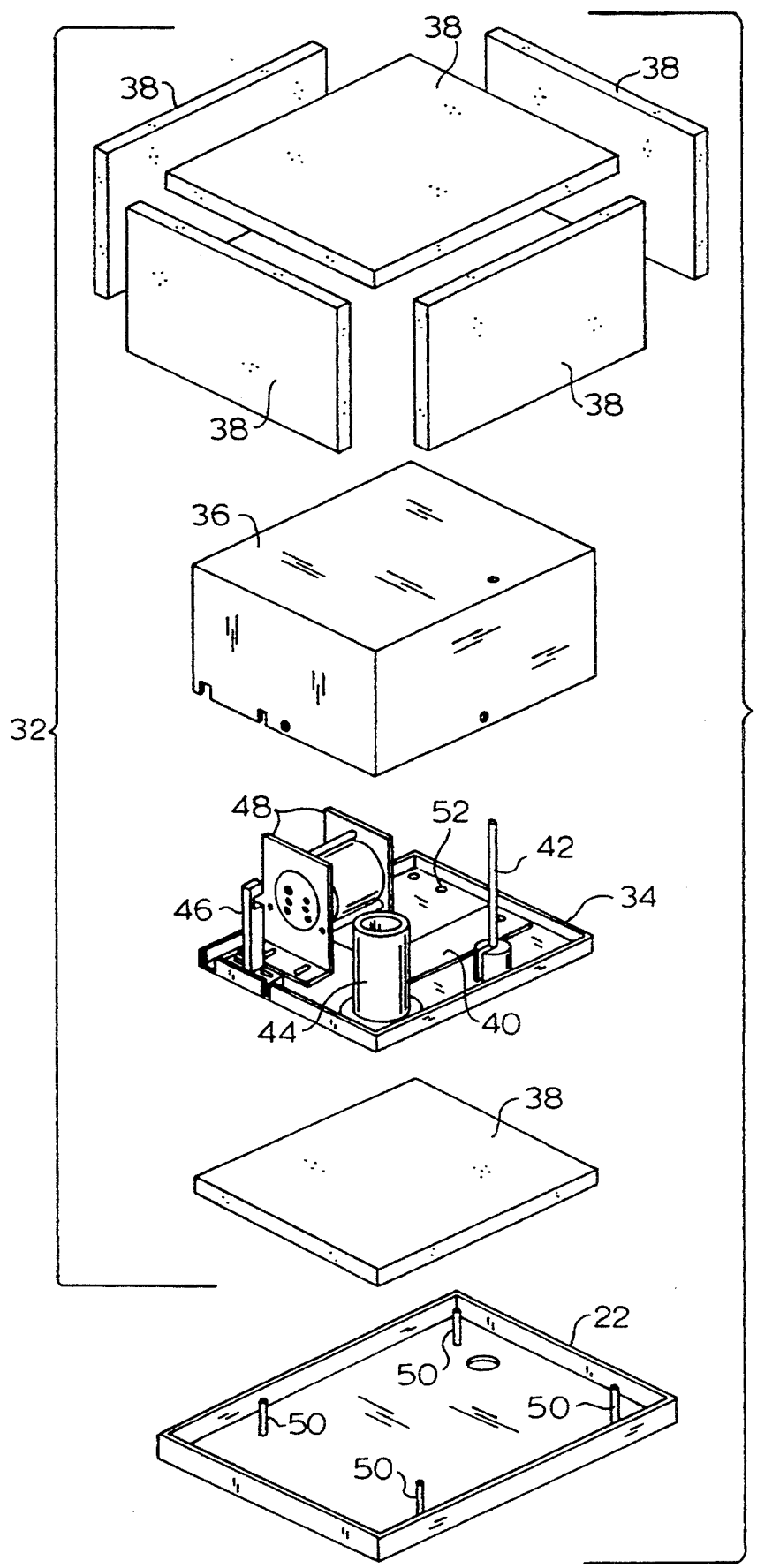
FIG. 5 is an exploded perspective view of a heated enclosure for the invention.

Heated oven enclosure 32 (FIG. 5) comprises a base 34 and a cover 36, each of which is covered externally with pieces 38 of ½-inch thick rigid insulation (½" Ceraboard 100 made by R. R. Horne & Co., Inc. Stone Mountain, Ga.). The enclosed volume is heated by a 125-watt strip heater 40 (No. S1J5U1, manufactured by Watlow Manufacturing Company, St. Louis, Mo.) which is mounted to oven base 34. A type K thermocouple sensor positioned inside the oven is used for temperature feedback. Base 34 of heated oven enclosure 32 also contains mounting hardware for a differential pressure switch bracket 42, an expansion volume bracket 44, a union elbow bracket 46, and a cryotrap assembly 48. Heated oven enclosure 32 mounts to cabinet base 22 by one-inch standoffs 50 preferably made of stainless steel or other material. The lower the thermal conductivity of the material, the less heat is transferred to the base of the cabinet enclosure. A 0.272 inch diameter hole 52 in base 34 of heated oven enclosure 32 provides an entrance for the analytical column to enter the enclosure and attach to the assist/column interface. Assist/column interface ("T" fitting) 96 (see FIG. 6) is mounted to the outlet of the primary collection trap, providing its only support.

The apparatus of the invention comprises a differential pressure switch 54 (FIG. 1) which allows gas to be sampled and analyzed by gas chromatography without encountering any surface in the apparatus except an inert surface or a surface which has been deactivated so that it is inert. Rather than use a conventional physical valve that reroutes flow mechanically, and as such, contains metal parts and deformable materials for gaskets, and the like, the system inlet comprises a linear volume with five specially placed gas flow ports that allow the sample flow and the helium carrier gas flow to be alternately introduced into the system through differential pressure control. There are no moving parts, metal surfaces or deformable materials in or surrounding the gas being sampled or transported in the apparatus.

Sample flow is established through some external means, for example, a 0.25 mm (I.D.) fused silica tube 18 inches long, which connects the sample container to the injection system, as is known in the art, in the range of approximately 50 to 250 ml/min. The apparatus and method of the invention do not require a specific flow rate, but only that there is excess flow detected at the "vent" port when the helium valve is in the "off" state. The upper limit may be empirically determined in a particular system by detection of sample infiltration into the helium carrier gas, or by a calculation of the approximate flow rate at which flow becomes non-laminar. For the geometry of the switch (0.75 mm I.D.), the theoretical limit as determined by a Reynolds number of 2000 is about 1100 ml/min. It is known in the art that above this Reynolds number, flow in a circular cross-section tube becomes turbulent. For a safety factor, to be sure that turbulent flow is avoided, a flow rate of 250 ml/min. is preferably chosen as the upper limit.

There are two competing factors which determine the preferable arrangement of differential pressure switch 54 for optimal operation. First, the distance between sample port 56 and helium port 58 should be as large as possible to avoid diffusion or turbulent mixing. Second, the overall dead volume should be as small as possible to assure precise and rapid flow switching. As discussed in more detail below, with the preferred injection tubing having an internal diameter of 0.75 mm, the adjustment is made in the length of differential pressure switch 54, particularly between the sample and helium ports. A minimum distance of ten internal diameters spacing has been empirically determined to be a reasonable compromise between these two factors. The preferred spacing for the preferred injection tubing is about 1 cm between the sample and helium ports. A greater spacing does not cause differential pressure switch 54 to cease working, but rather, increases the dead volume and thus affects switch precision without appreciable benefit in discrimination against sample/helium mixing. Reducing this spacing is beneficial for precise injection control especially for high concentration samples; however, the reduced spacing requires greater helium flow to keep the sample from infiltrating into the system and thus increase overall helium consumption.

Figure 1:
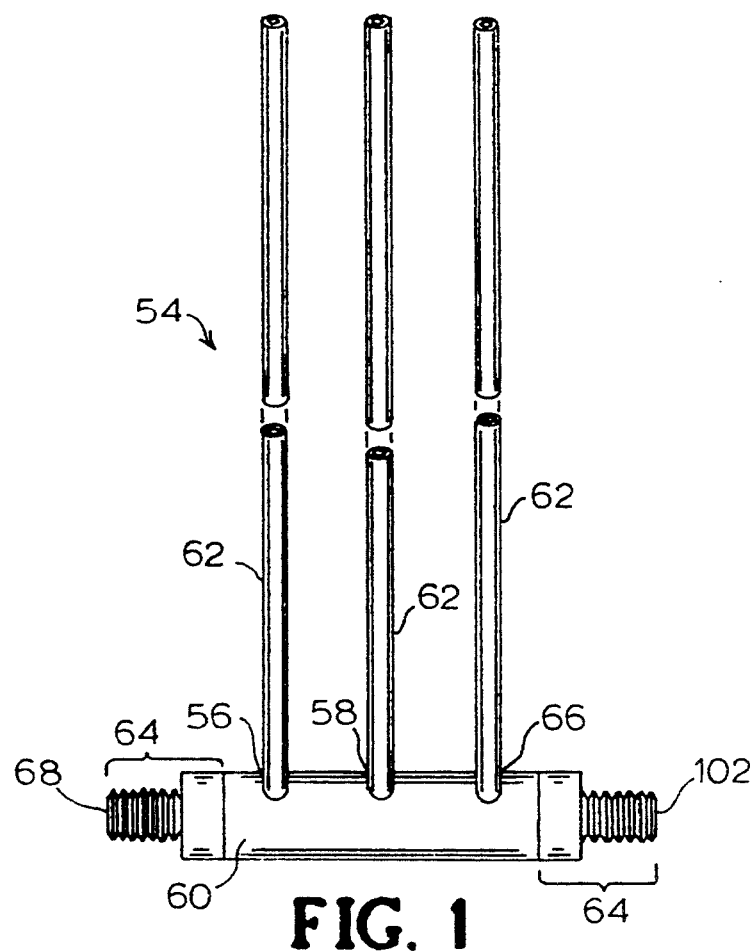
FIG. 1 is a perspective side view of a differential pressure switch as used in the invention.

Differential pressure switch 54 is held in place on heated oven base 34 by a machined aluminum bracket 42. The construction of differential pressure switch 54 (FIG. 1) consists of a piece of 0.3125 inch diameter T316 stainless steel rod 60 (commercially available) cut to 1.164 inch in length as the body of the switch. A hole is drilled through the center of the rod to give an inside diameter of 0.125 inch. Three holes with a 0.063 inch diameter are drilled perpendicular to the axis of the rod from the outer diameter to the inner diameter. The middle of these three holes is located in the center of the 1.164 length with each of the two other holes offset on each side of the middle hole by 0.394 inch (1 cm). Three pieces of identical 1/16-inch chromatography grade stainless steel tubing 62 (Model No. T316 SMLS, 0.0625 inch (O.D.)×0.030 inch (I.D.) tubing made by Handy & Harmon Co., Philadelphia, Pa.) twelve inches in length are each inserted into one of the three holes in the rod at a depth flush with the inside diameter of the rod. Tubes 62 are attached to rod 60 by silver solder. Two 1/16-inch stainless steel caps 64 (Part No. SS-100-C, Swagelok Co, Solon, Ohio) as shown in FIG. 1, drilled through in the center with a 0.063-inch diameter hole are attached to each end of rod 60 by a heliarc weld. These caps provide exits from the switch for the vent flow and assist/column flow, as well as providing 1/16-inch SWAGELOK TM fitting threads for interface connection purposes. The internal surface area of the rod assembly is preferably coated with deactivated fused silica (Restek Corporation) to provide an inert inner surface.

Figure 6:
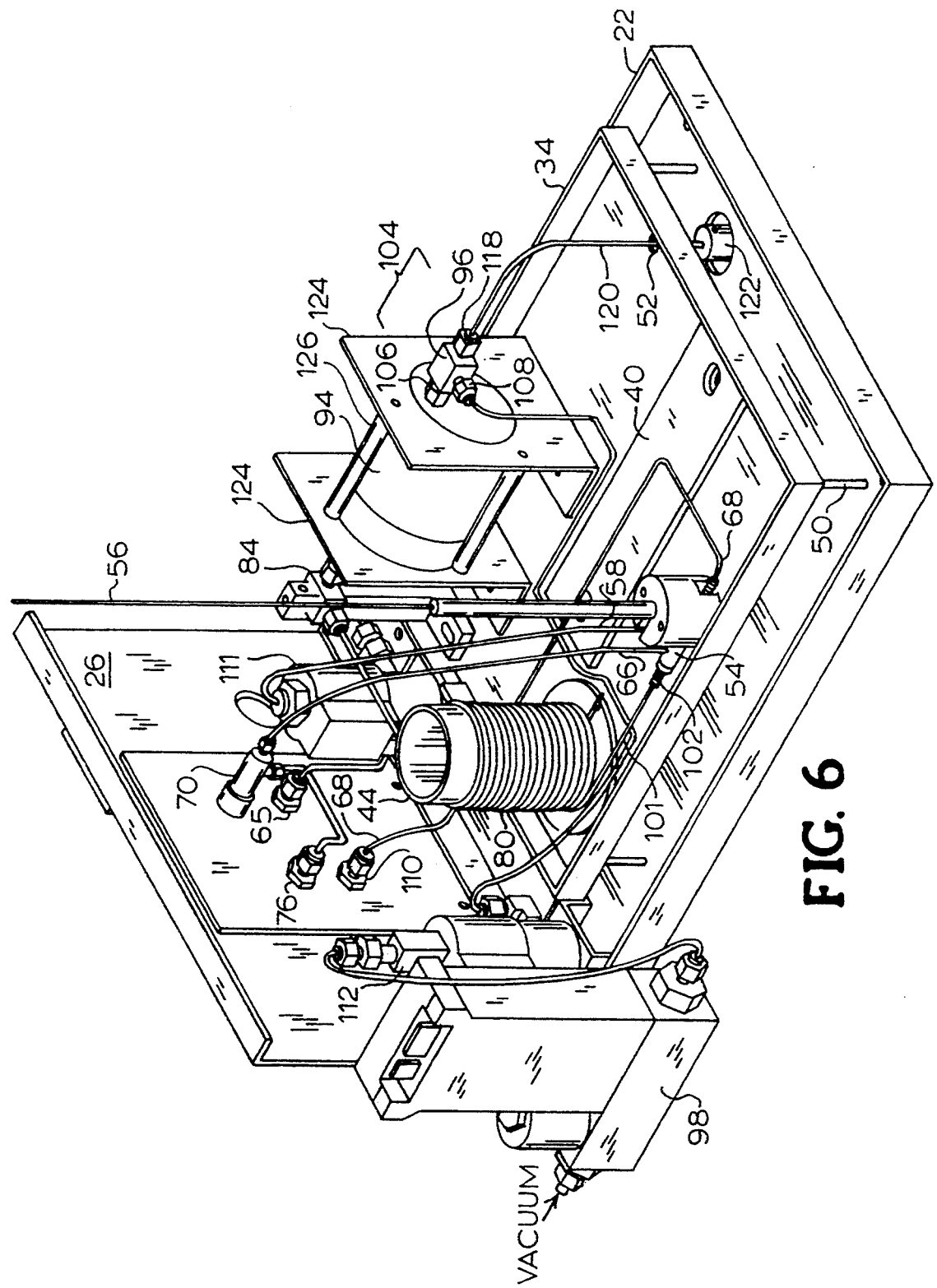
FIG. 6 is a perspective view of a portion of the apparatus of the invention.

The helium flow path enters the cabinet enclosure through a 1/16" bulkhead fitting 65 (Part No. SS-100-61, Swagelok Co., Solon, Ohio) mounted on the cabinet rear panel. The bulkhead fitting connects to the inlet of a two-way solenoid valve 111 (Part No. 51ZOO520KM, Peter Paul Electronics Co., Inc., New Britain, Conn.) which is normally open. The valve outlet connects to the center tube inlet 58 of differential pressure switch 54, which is formed with a 90-degree angle to remain inside the heated oven (FIG. 6).

Preferably the invention also includes a sweep flow port 66. Sweep flow port 66 allows cleaner, more rapid switch operation which is particularly important for the analysis of very high concentration samples. In addition, the use of sweep flow port 66 reduces the effective dead volume of differential pressure switch 54, which makes the overall system less susceptible to error induced by the mixing zone at the sample/helium flow interface for both high and low concentrations of analytes. Finally, for applications involving collection of a sample from the surrounding air or from a chamber at atmospheric pressure, the sweep flow provides the mechanism for delivering sample to the system. In such cases, vent port 68 must be blocked, for example, by using a SWAGELOK TM plug fitting (Model No. B-100 for brass or SS-100-P for stainless steel of Swagelok Co., Solon, Ohio, or other 1/16 O.D. plug) which is attached to the vent bulkhead fitting on the rear panel. Since there is no pressure differential between the sample and the vent line which is at atmospheric pressure, vacuum must be used to pull the sample into the switch. The vent must be plugged so that the sample will not be diluted with flow being pulled in through the vent line. The assist flow pulls the sample through the system and through assist valve 112, and the sweep flow provides the assist flow plus excess flow to eliminate the switch dead volume.

The sweep flow exits differential pressure switch 54 through the rear tube and connects to the inlet of a 1/16" fine metering valve 70 (Part No. SS-SS1-A, Nupro Co., Willoughby, Ohio) mounted on cabinet rear panel 26. The outlet of the valve connects to a 1/16 bulkhead-tube fitting (not shown)(Part No. SS-100-61, Swagelok Co, Solon, Ohio) also mounted on rear panel 26. The bulkhead fitting connects to vacuum ballast 74 shown in FIG. 8 (for example, Part No. 8548.80V1000, Graseby Nutech).

The sample flow enters the switch through the front tube or sample flow port 56. This tube protrudes through the top of the oven and cabinet allowing for the interface to the sample source.

The vent flow exits differential pressure switch 54 through the forward horizontal tube fitting (vent port 68) and connects to a 1/16 bulkhead union 76 (Part No. SS-100-61, Swagelok Co.) mounted on cabinet rear panel 26.

Primary collection (cryogenic) trap 78 and expansion volume 80 (FIG. 6) are composed of 0.75 mm I.D. tubing internally coated with deactivated fused silica. These two components may either be constructed in one piece or be separately constructed and jointed with a similarly coated junction to allow easy replacement of the trap for maintenance. Expansion volume 80 provides a fixed volume into which the gas may flow.

A first purpose of expansion volume chamber 80 is to serve as a heated inert transfer line of sample to primary collection trap 78, and to isolate the trap temperature from differential pressure switch 54, particularly when the trap is at the cold set-point. A second purpose of expansion volume 80 is to serve as a linear reservoir for the sample when condensed water, $CO_2$, or other major components of the sample expand more rapidly than the column flow into the analytical system can accommodate. Expansion volume 80 remains at the internal temperature of the differential pressure switch 54, while primary collection (cryogenic) trap 78 (FIGS. 3A and 8) is cooled for sample concentration, and then heated. Having two separate pieces allows the trap to be changed independent of the expansion volume.

The geometry of expansion volume 80 is the same as that of the trap 78 to minimize dilution with infiltrating helium from the switch. The volume is chosen to accommodate about 0.5 ml of back flow during desorption which occurs when the primary collection trap is heated to vaporize the condensate. This configuration takes into consideration the removal rate of condensate from the trap, the temperature ramp rate during desorption, and the thermodynamics of the volatilization of the primary trapped component of most samples, water.

A longer (larger volume) expansion volume would serve the same purpose but would be more cumbersome, and a shorter (smaller volume) would be more likely to lose sample through the switch vent.

Figure 2:
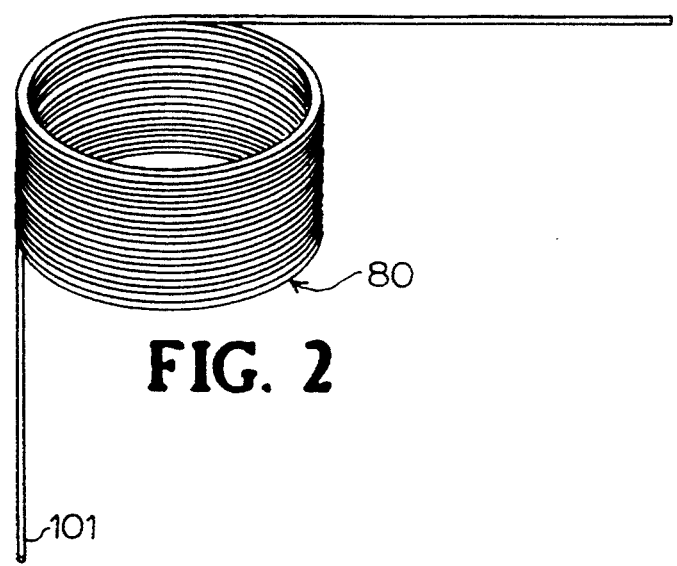
FIG. 2 is a perspective view of an expansion volume chamber as used in the preferred embodiment of the invention.

Expansion volume 80 and primary collection trap 78 of the preferred embodiment of the invention are coiled as shown in FIGS. 2 and 3A, respectively, to conserve space and simplify temperature control.

Sample expansion volume chamber 80 is held in place by expansion volume bracket .44 mounted to oven base 34. Expansion volume chamber 80 consists of a 96-inch length of 0.0625-inch outside diameter (O.D.), 0.030-inch (I.D.) T316 chromatography grade stainless steel tubing (Handy and Harmon T316 SMLS 0.0625×030″ tubing). The tube is coiled into 19 coils having the orientation shown in FIG. 2. An inner coil diameter of the expansion volume of about 1⅜ inch with approximately 19 coils provides sufficient volume for most analyses. The internal surface of the tube is coated with deactivated fused silica for inertness (Restek Corporation). This size was determined based on the requirements discussed herein in the discussion of the primary collection trap and expansion volume.

Enclosure pieces 94a,b for primary collection trap (FIGS. 3A-3D) are designed to evenly cool the trap tubing through use of a specialized distributive flow pattern of the metered liquid/gaseous nitrogen cryogen. The specific design is not critical to the overall operation of the apparatus and method of the invention; however, the compact nature and precise performance of this design is a great advantage over other conventional hardware. The heating pattern during desorption is particularly important. The trap tubing in the preferred embodiment is in thermal contact with a specifically formed aluminum rod 88 that contains the heater assembly in such a way that the upstream portion of the trap is heated more quickly than the downstream portion (FIG. 3A). This helps to maintain the bandwidth of the injection volume at a minimum. Though not critical to the operation of the system, this feature helps improve overall performance of the invention.

Primary collection trap 78 consists of a 13-inch length of 0.0625 inch O.D., 0.030 inch I.D. T316 chromatography grade stainless steel tubing (Handy and Harmon T316 SMLS 0.0625×030″ tubing). The tube is coiled three complete revolutions with a 1-inch coil inside diameter. An inner coil diameter of about 1 inch is sufficient for adequate cryogenic concentration of most samples. The equal lengths of excess tubing on each side of the coils are bent with a 0.500 radius r perpendicular to the trap coils (FIG. 3A). Side top 86 of the outlet tube from primary collection trap 78 is beveled (FIG. 3A) to allow increased "assist" flow rates from the outlet tube into the assist flow "T" fitting 96. The internal surface area of primary collection trap 78 is coated with deactivated fused silica for inertness. Coiled primary collection trap 78 is mounted on the outer surface of a machined aluminum rod 88 which contains heater 90 (150 watt ¼-inch O.D. cartridge heater, Watlow No. E1A53) and type K thermocouple sensor. Rod 88 also contains a 0.125 inch diameter hole (not shown) that allows liquid nitrogen (LN2) to enter the trap assembly for cooling. Heater 90 is positioned at the sample inlet end of rod 88.

Primary collection trap 78 is enclosed by a two-piece TEFLON™ housing 94a,b that provides heat zone isolation from the heated enclosure. Housing 94a,b forms a leak-tight seal for the LN2 gas used for subambient cooling. Housing 94 is machined from commercially available 2-inch diameter TEFLON™ rod (FIGS. 3A-3D). Each housing piece 94a,b has a hole 93 for the tubing to go through. Additional holes 92 are placed in one of housing pieces 94a for liquid nitrogen to cool primary collection trap 78. The two pieces of the enclosure are held together by two stainless steel brackets 124 (FIG. 6) connected by three 0.250-inch O.D. stainless steel tubes 126 (FIG. 6).

The assist flow of the apparatus of the invention allows a sample collection flow that is greater than the column flow that is always sweeping the trap, while maintaining the overall design criterion of avoidance of valves and valve surfaces. The assist flow connection is made at the outlet of the primary collection trap 78 in a "T" fitting 96 (FIG. 6) that is internally coated with deactivated fused silica. This flow is precisely set through a mass flow controller 98 (for example, Model 201-AFASVBAA, Porter Instrument Company, Hatfield, Pa.) and is turned on and off through a computer controlled valve 112 (see FIGS. 6 and 8). Although the connection of valve 112 to controller 98 is shown as a direct connection for schematic purposes in FIG. 6, the preferred connection utilizes a fitting mounted on rear panel 26. The assist flow is set to an appropriate value to maximize sample consistency throughout yet avoid trap breakthrough of the very volatile VOCs. For the preferred configuration, an assist flow of 20-30 ml/min is appropriate.

An important parameter of the assist flow is the on-/off timing. During the desorption of primary collection trap 78, the assist flow is in the off state to assure that all of the sample is transferred to the analytical system. After analytes are transferred, the assist flow is reestablished. This sweeps away any remaining water vapor and unwanted heavy organic compounds that may have become entrained in the system. For most of the applications of this system, such as those discussed herein, the assist flow is a necessary feature. Helium flow from a helium source (not shown) is activated by helium valve 111.

Figure 7:
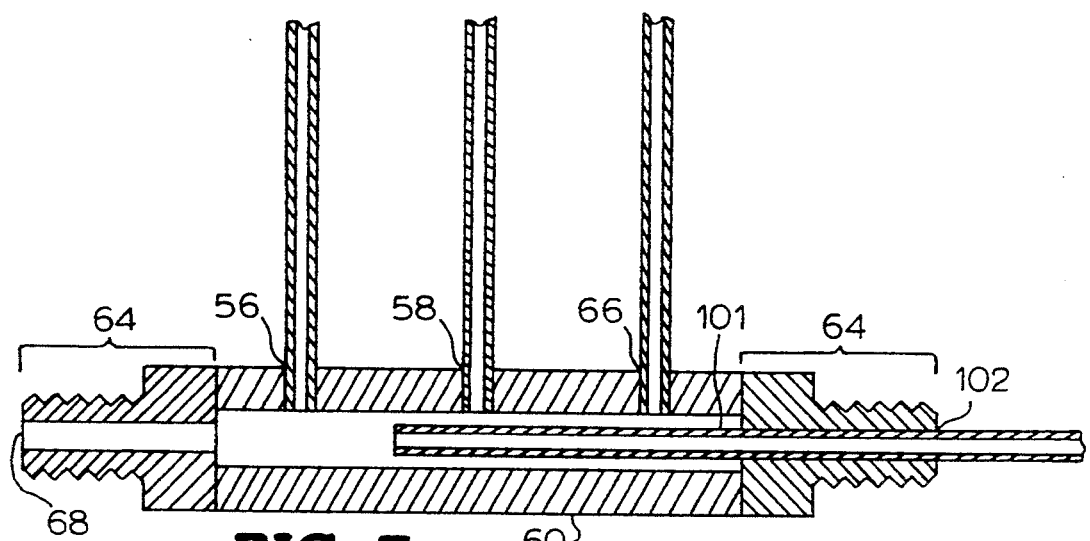
FIG. 7 is a linear section of a differential pressure switch according to the invention.

Assist/column connection 102 (FIG. 6) is the interface of differential pressure switch 54 to expansion volume chamber 80. Expansion volume inlet 101 is inserted through assist/column flow tube fitting 102 until the end of expansion volume tube 80 is equidistant between the helium and the sample inlets of differential pressure switch 54 (FIG. 7). Expansion volume chamber 80 connects to the inlet of primary collection trap 78 by a union elbow tube fitting 84 (Part No. SS-100-9, Swagelok Co.) which is internally coated with deactivated fused silica.

Assist/column interface 104 connects to the outlet of primary collection trap 78. Interface 104 consists of a union "T" 96 derived from a ⅛-inch GC connector kit (Part No. 14183, Alltech Associates, Deerfield, Ill.) in which the stainless steel stem is removed. The wide bore side 106 of the straight through path connects to the outlet of primary collection trap 78. The assist flow path splits from the column path through the 90-degree arm 108 of "T" 96 and connects to a 1/16-inch bulkhead tube fitting 110 (Part No. SS-100-61, Swagelok Co.) mounted on cabinet rear panel 26. Bulkhead fitting 110 connects to the inlet of a 2-way normally closed solenoid valve 112 (Peter Paul No. 52H8DGB). The outlet of valve 112 connects to a 100-cc/min. mass flow controller 98 (Porter Model 201-AFASVBAA)(FIG. 6). The outlet of mass flow controller 98 connects to a ¼-inch "T" tube fitting 114 which connects to vacuum ballast 74 which connects to vacuum pump 116 for a stable vacuum source (FIG. 8).

Third arm 118 of assist/column interface 104 connects the injection system to the secondary refocusing trap 122, which is mounted below the injection system.

Figure 9:
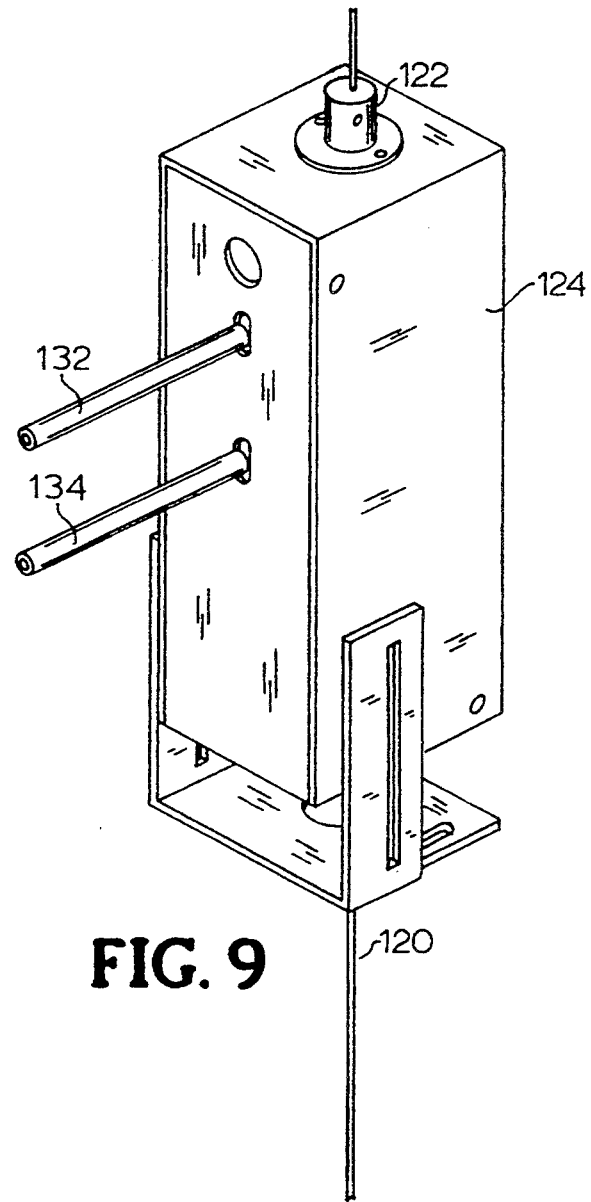
FIG. 9 is a perspective exterior view of the secondary refocusing trap and an enclosure which may be used with the invention.
Figure 10:
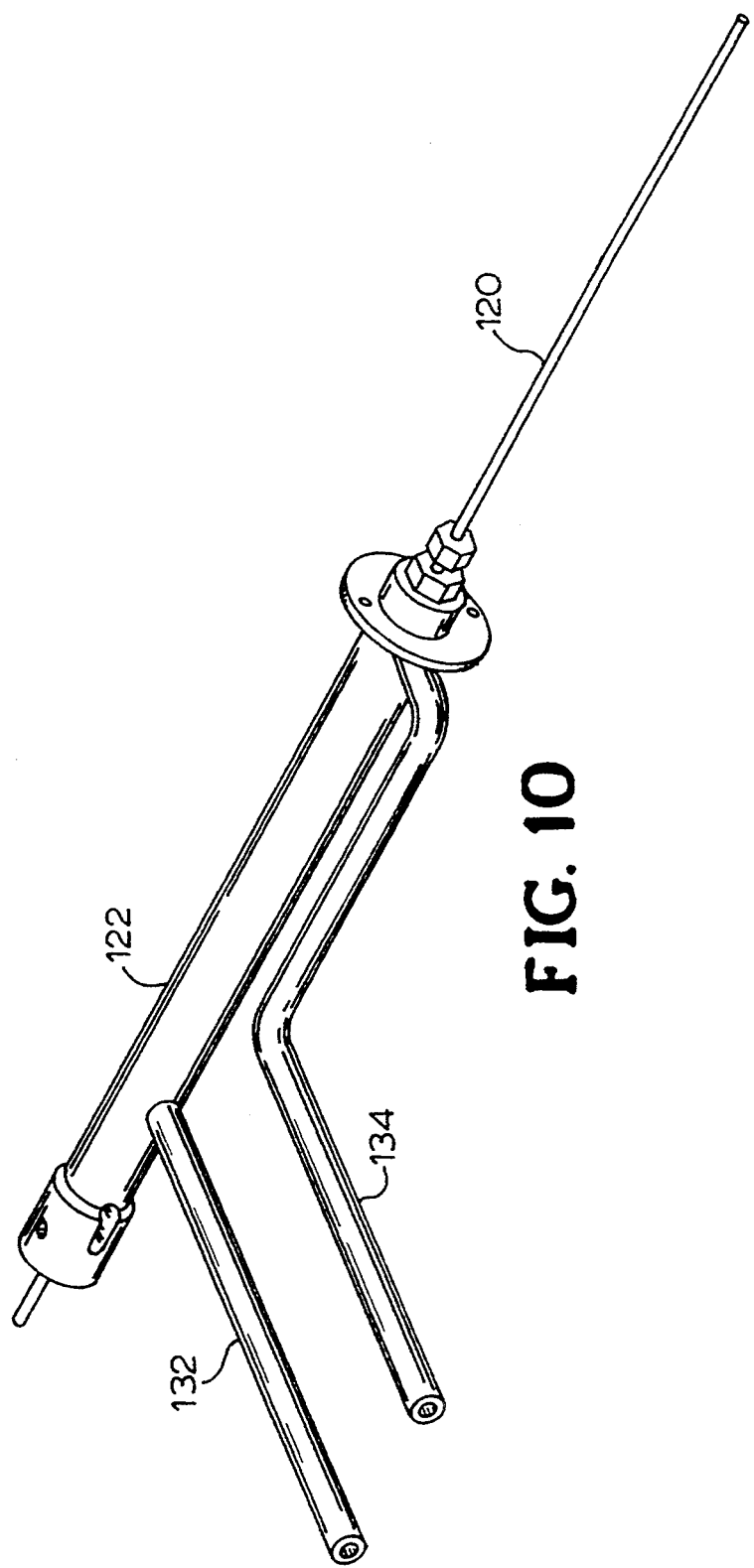
FIG. 10 is a perspective view of the tubing of the secondary refocusing trap.
Figure 11:
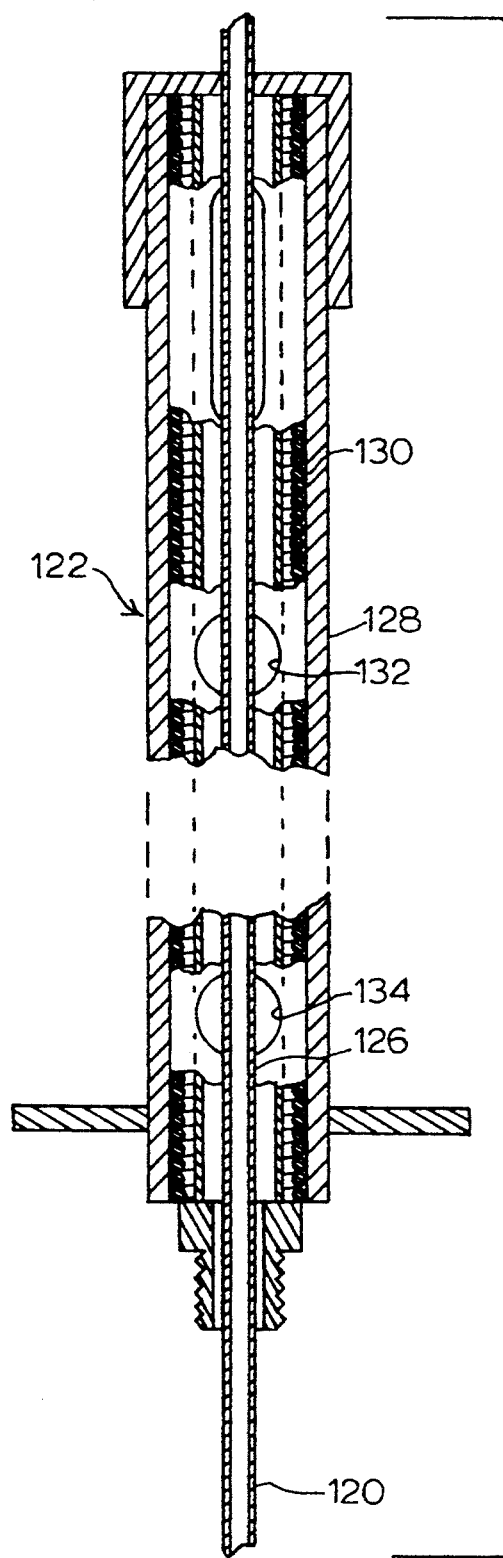
FIG. 11 is a cross-sectional view of the secondary refocusing trap.

Secondary refocusing trap 122 (for example, Part No. 354A, Graseby Nutech)(FIGS. 9–11) is used as a secondary trap to refocus the sample into a very small volume on column 120 or a precolumn. Secondary refocusing trap 122 is mounted inside a rectangular housing 124 (FIG. 9) and comprises an inner tube 126 and an outer tube 128 (FIG. 11). A coiled heater 130 is coiled about the inner tube 126 without touching it, inside the outer tube 128. During the cooling cycle, liquid nitrogen (LN2) enters an entry tube 132 (see FIG. 10) at the top of secondary refocusing trap 122, and goes into the space between the inner and outer tubes. The LN2 exits by means of an exit tube 134 which carries the LN2 from the lower area between the inner tube and the outer tube away from secondary refocusing trap 122. Secondary refocusing trap 122 is used in the invention to avoid some common capillary column chromatographic problems often encountered in the presence of excess water vapor. Such problems include multiple peaks, peak broadening, and peak tailing. Secondary refocusing trap 122 allows achievement of sharp, well-shaped GC peaks of the very volatile compounds. For small sample volumes, or samples with very high concentration compounds, secondary refocusing trap 122 may be redundant with primary collection trap 78. For most applications, however, secondary refocusing trap 122 is necessary to achieve reliable chromatography and quantitation. In any case, having secondary refocusing trap 122 as part of the apparatus, allows the operator to analyze a variety of samples whether or not secondary refocusing trap 122 is necessary for a particular sample.

Secondary refocusing trap 122 receives analytes from primary collection trap 78 in a helium matrix with the $CO_2$ and a portion of the water vapor already removed. The tubing material of secondary refocusing trap 122 may thus be smaller than that of primary collection trap 78, for example, 0.53 mm I.D. Secondary refocusing trap 122 is rapidly heated to inject a tight bandwidth of sample to the gas chromatograph. Secondary refocusing trap 122 uses LN2 to reach subambient temperatures. A 0.040-inch I.D. tube travels through the center of the unit and contains the column. This provides a shield for the column from potential damage caused by the pressurized LN2. External secondary refocusing trap 122 contains a nickel 200 tube (0.0625 inch O.D.×0.040 inch I.D.) that begins at the top of secondary refocusing trap 122, runs through the center of trap 122, and out the bottom of trap 122, extending an additional length (typically 6 inches) out the bottom of trap 122. The nickel tube is contained in another tube (preferably with a ⅜-inch O.D) which is sealed at its outer diameter at the top and the bottom of secondary refocusing trap 122. This allows liquid nitrogen to flow around the outside of the tube, but not touch the inside. The trap is typically mounted to the top of the gas chromatograph by a mounting bracket with the bottom of the trap close enough to the top of the gas chromatograph that the tube extends through the top of the gas chromatograph and into the gas chromatograph oven. The gas chromatograph analytical column is fed up into the tube of the secondary refocusing trap before the column enters the secondary refocusing trap.

Gas Flow Parameters

As discussed above, there are six gas flow parameters in the preferred embodiment of the invention: the sweep flow, assist flow, helium flow, column flow, sample flow and vent flow. The sweep flow, which is the flow of helium and sample when both are flowing from the differential pressure switch to a metering valve. The sample and helium are pulled through the switch with a vacuum to prevent back diffusion of the sample. The sweep flow is set between 10 and 30 ml/min, while there is excess helium purging the switch. This may be fine-tuned later based upon need as discussed herein. The assist flow, which is the flow of helium or the sample, depending on the stage of the method of the invention, from the differential pressure switch through the expansion volume and trap, and out the assist "T" of the assist/column interface is set to achieve the required sample volume in a reasonable sample trapping time (t). For this configuration, 10–35 ml/min is appropriate. The total volume trapped in time t is the sum of the column flow and the assist flow times t. The helium flow, activated by helium valve 111, is set so that there is between 20 and 100 ml/min excess flow measured at the vent under the conditions when sample port 56 is capped (no sample is entering the port at this point), the assist flow is on, and the sweep flow is on. The exact helium flow is adjusted in conjunction with all the other settings. For example, with assist flow at 20 ml/min, sweep flow at 29 ml/min, column flow at 1 ml/min and a vent flow of 50 ml/min, the helium flow would be 100 ml/min.

The column flow is generated by the MS vacuum system through the direct column GC/MS interface. The exact value is determined by the column configuration. A typical 30 meter by 0.32 mm I.D. column will have a column flow of about 2 ml/min helium at 5° C. The exact column flow can be determined by calculation using the volume of the column and the elution time of an air peak. The sample flow is set external to the system. As discussed herein, the system is designed for a range of sample flow of 50–250 ml/min. Sample flow must be greater than the combined total of the assist flow plus sweep flow plus column flow so that only the sample is trapped when the helium switch is off. The maximum supply flow can be determined empirically by increasing sample flow and monitoring air infiltration in the switch as a mass spectrometer (MS) response. When nitrogen and oxygen appear in excess above background in the MS, sample flow is too high.

The vent flow is monitored periodically in two configurations: (a) helium on, sample on, assist on, sweep on; or (b) helium off, sample on, assist on, sweep on. The vent flow should always be positive (flowing out of the system) unless the sweep is being used to pull an ambient pressure sample from the air or a chamber. In such a case, the vent port is capped.

In operation of the apparatus of the invention when concentration is required for low level samples, primary collection trap 78 is cooled cryogenically to a well controlled set-point and serves as the analyte concentration zone as in prior cryogenic concentrators, where nitrogen and oxygen are removed from the sample, and $CO_2$ is partially removed from the sample. The internal diameter (0.75 mm) determines the overall geometry of the whole injection system from a chromatographic standpoint and from construction considerations. Other inside diameters are possible and have been tested with good results. Experimental analysis reveals, however, that an I.D. of 0.32 mm is essentially too narrow to accommodate typical air samples (100 ml to 500 ml volume) and still avoid blockage due to ice formation during the collection phase. An I.D. of greater than 0.75 mm is likely to have breakthrough of the very volatile analytes as the surface to volume ratio decreases (proportionately to 1/radius) for the same length of tubing. This decreases the probability for capturing a particular molecule.

The computer system used to control the various valves and switches of the invention and to provide the operator with information on the status of the system may be any as are known in the art, for example, the Model 2000 controller (Graseby Nutech) having a serial interface to a compatible computer.

The apparatus and method of the invention allow high level processing for VOCs (i.e., for concentrated samples having high levels of VOCs) in analysis of wastes, product head space, soil gas, etc. Based on the inherent inertness of the system, which avoids analyte adsorption, chemical reaction, or permeation into the surfaces, there may be a rapid switching of the helium valve from off to on and back off, for example, to determine the injection bandwidth. The injection bandwidth is determined by the amount of time that the helium is not flowing, i.e., when the helium is flowing the sample is pushed out the vent and is not analyzed by the gas chromatograph. Critical parameters to allow accurate and complete analysis in these circumstances include the dead-volume of the switch, which determines the minimum injection bandwidth, run to run helium flow stability, inside diameter of the expansion volume and the initial trap, sweep flow stability, and assist flow rate and stability.

The apparatus and method of the invention may also be used for trace-level and ultra trace-level VOCs measurement for a wide variety of VOCs and polar VOCs. This includes applications where the Environmental Protection Agency (EPA) has guidance criteria or standards and minimum levels for particular compounds such as air toxics, ozone precursors (excluding C2 hydrocarbons) and odors analysis. This type of measurement is also appropriate for other air matrices such as in exposure chambers for materials offgas testing. Critical parameters in adjusting the apparatus of the invention for this use include system cleanliness, thermal zone stability to allow precise concentration and injection of large air volumes. The "assist flow" feature of the apparatus and its on/off control are important in allowing rapid trapping without desorption losses.

A third major application of the apparatus and method of the invention is the area of exhaled breath analysis for mid-level and trace-level VOCs, with special emphasis on polar VOCs. High levels of $CO_2$ and $H_2O$ in breath, as well as the mixture of relatively high acetone, ethanol, and isoprene levels, together with trace-level compounds of interest, make this a difficult matrix for analysis. Critical parameters include the overall inertness of the system to allow difficult (reactive, adsorptive) compounds to be transferred, insensitivity of chromatographic injection to water disruption (as provided by a refocusing trap) and overall capacity to focus both high and low level concentration simultaneously without loses (as provided by the trap/expansion volume design).

The features and advantages of the present invention will be more clearly understood by reference to the following examples, which are not to be construed as limiting the invention.

EXAMPLES

EXAMPLE I. Concentration of a Low Level Sample

Upon the start of a sample concentration sequence, the injection system performs an initialization. The oven enclosure, primary collection trap (Cryotrap), and secondary refocusing unit are all at their elevated temperature set-points (each at 100° C. for example) The helium valve is set at "off" which means that the valve is allowing helium to flow, since it is a normally open solenoid valve. The assist valve 112 is on, which allows assist flow of helium to flow through the assist valve, which is a normally closed solenoid valve. This assist flow is flow-regulated by the mass flow controller positioned between the assist valve and the vacuum ballast (see FIG. 8). When this initialization is complete, as determined by the solenoid valves set to the proper state, and the temperature zones are at setpoint, the system prompts the operator to begin the concentration process when ready.

Once initiated by the operator, the system performs a helium purge of the Cryotrap at the current elevated temperature to flush anything remaining in the Cryotrap out of the system.

The Cryotrap is cooled to a subambient temperature for the concentration process (typically −150° C.). When the Cryotrap reaches the desired set-point and is stable at that temperature, the operator is prompted by the status line on the computer display to open the sample container in which the sample was originally collected. The operator opens the sample container and waits 30 seconds for the sample to displace all air in the sample line. This results in both the helium flow and sample flow entering the differential pressure switch. The concentrator is in a wait state in the concentration process while the operator performs these manual operations. When the operation resumes the concentration process, the helium valve is turned "on" thus shutting off the helium flow into the switch.

The assist flow pulls the sample through the cool Cryotrap until the desired volume has been trapped based on the integrated flow from the mass flow controller controlling the assist flow. Once the concentration is complete, the helium valve is turned off allowing the helium flow into the differential pressure switch, the Cryofocus unit begins cooling, and the operator is prompted to close the sample container, removing sample flow from entering the differential pressure switch, and preserving the remaining sample in the sample container. The helium flow flushes any balance gas remaining in the Cryotrap out of the assist flow for 60 seconds. This also gives the Cryofocus time to reach its subambient set-point. Next the assist valve is turned off, stopping the assist flow and diverting 100 percent flow to the column. The Cryotrap is heated to an elevated temperature which transfers the concentrated sample to the Cryofocus unit. Once this transfer has taken place, the Cryofocus is heated to an elevated temperature (typically 150° C.), and the GC analysis is started. The assist valve is turned on to clean up any remaining material in the Cryotrap. This completes the concentration and injection process and the system waits for the time necessary for sample analysis, before it initializes for the next injection.

EXAMPLE II. Injection of a High Level Sample

Upon the start of a high level sample injection sequence, the injection system performs an initialization, setting the appropriate valve states, temperature zone setpoints, and flow control setting as follows. The helium valve is set to "off" which allows helium flow through this valve, and the assist valve is set to "off", shutting off the assist flow through this valve. The sweep flow is always on.

The temperature zones, oven enclosure, primary collection trap, and secondary refocusing trap are typically set to 100° C. The flow controller that controls the assist flow is set to 0-flow (off). After these initialization steps are completed the system prompts the operator to begin the injection process by displaying a message on the computer display.

Unlike the low level sample example in which the primary collection trap is cooled at this point, this trap remains hot at all times. The secondary refocusing trap is not required for this sequence, but use of the secondary refocusing trap is encouraged to significantly improve the injection system performance. The secondary refocusing trap is cooled at this time with a typical setpoint of −190° C.

The operator opens the sample container and waits typically 30 seconds for the sample to displace all air in the sample line. At this point, both helium and sample are entering the differential pressure switch. Because of the switch structure, only helium makes up the column assist flow and sweep flow. All of the sample flow and the balance of the helium flow exit the differential pressure switch out of the vent port. When the operator resumes the sequence, the helium valve is turned "on", shutting off helium from entering the differential pressure switch. The "on" time specified by the operator is a variable set before the start of the operation and depends on the injection volume desired. When the helium flow is stopped from entering the differential pressure switch, only the sample flow remains, thus accounting for the makeup of the sweep and column flows at this point. The injection volume is determined by the product of column flow rate and the time duration that the helium valve is "on". While the helium flow is shut off, the sample is being concentrated on the secondary refocusing trap. After the time delay is complete, the helium valve is turned "off" allowing flow to the switch. The helium flow flushes the sample that has not yet reached the secondary refocusing trap and also purges the column of the balance gas of the sample obtained during the injection. After a time delay for this purging to occur (about 2 minutes), the secondary refocusing trap is heated (for example, 150° C.) and the gas chromatographic analysis is started. This completes the injection process and the injection system waits for the time necessary for the sample analysis, before it initializes for the next injection.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method for analyzing a sample for volatile organic compounds, comprising:
   (a) providing an apparatus comprising a hollow differential pressure switch having:
      (i) a central helium port connected to a source of helium,
      (ii) a sample flow port on a first side of said helium port,
      (iii) a sweep flow port on a second side of said helium port,
      (iv) a vent end, and
      (v) an assist/column flow end; wherein said differential pressure switch has an interior surface which is inert;
      (vi) an oven enclosure, a primary collection trap, a source of helium, a mass flow controller for controlling gas flow through an assist valve;
   (b) connecting said apparatus to an analytical column of a gas chromatograph;
   (c) initializing the apparatus by elevating the temperature of said oven enclosure and primary collection trap with the helium flowing in the apparatus and no sample flowing;
   (d) performing a helium purge of the primary collection trap at a hot temperature;
   (e) cooling the primary collection trap to a subambient temperature to enable sample concentration;
   (f) opening a sample container into said sample port, and allowing the sample to displace air in a sample line extending from said sample container to said sample port;
   (g) turning off the helium flow;
   (h) when concentration of said sample is complete, turning on the helium flow for helium flow to displace gas remaining in the primary collection trap, leaving condensate on the collection trap, while the collection trap continues cooling;
   (i) closing the sample container;
   (j) turning off the assist valve so gas flow is to the analytical column;
   (k) heating the primary collection trap to an elevated temperature to transfer concentrated sample to the analytical column; and
   (l) analyzing said sample using said analytical column, wherein sample flow may be switched without mechanical means, wherein said method utilizes selected timing and temperature parameters for each said sample, and wherein the gas chromatograph and apparatus may be used with samples having anywhere from very high to very low levels of volatile organic compounds by changing timing and temperature parameters and by changing gas flow through the pressure switch non-mechanically, without changing anything else mechanically.

2. A method according to claim 1, wherein said interior surface comprises a coating of fused silica so that gas flowing through said differential pressure switch is only exposed to surfaces of fused silica.

3. A method according to claim 1, further comprising providing a secondary cryogenic focusing unit, and heating said unit to an elevated temperature, so that sample in said heated primary collection trap is transferred to said unit, prior to analysis by gas chromatography.

4. An apparatus for connection to an analytical column of a gas chromatograph for analyzing samples for volatile organic compounds, comprising a differential pressure switch having a hollow interior and a plurality of ports, wherein sample flow may be switched without mechanical means, and wherein the gas chromatograph and apparatus may be used with samples having anywhere from very high to very low levels of volatile organic compounds by changing timing and temperature parameters and by changing gas flow through the pressure switch nonmechanically, without changing anything else mechanically, and wherein the hollow interior of said differential pressure switch has interior surfaces which are inert so that gas flowing through the ports and hollow interior of said apparatus from a sample port to said analytical column is only exposed to inert interior surfaces.

5. An apparatus according to claim 1, wherein said plurality of ports of said differential pressure switch comprises:
 (a) a central helium port,
 (b) a sample flow port on a first side of said helium port, and
 (c) a sweep flow port on a second side of said helium port, wherein each of said .ports extends from said hollow interior to outside said differential pressure switch; wherein said hollow differential pressure switch further comprises:
 (a) a vent end on a first end of said differential pressure switch, and
 (b) an assist/column flow end on an end of said differential pressure switch opposite said vent end.

6. An apparatus according to claim 5, further comprising:
 (a) a hollow expansion volume chamber comprising:
  (i) an inlet tube, which is inserted through said assist/column flow end and extends to halfway between said helium port and sample port,
  (ii) a piece of tubing having a plurality of coils, and
  (iii) an outlet tube;
 (b) a hollow primary collection trap comprising a piece of tubing coiled about a rod, said rod comprising:
  (i) an entry port for a cryogenic substance,
  (ii) an inlet end,
  (iii) a heater at said inlet end, and
  (iv) an outlet, wherein said expansion volume chamber outlet tube connects to the primary collection trap inlet end; and
 (c) a hollow assist/column interface comprising:
  (i) an inlet end connected to the outlet of the primary collection trap;
  (ii) an arm connected to a mass flow controller valve and vacuum system; and
  (iii) an outlet end connected to the analytical column, wherein said expansion volume chamber, said primary collection trap, and said assist-/column interface also have interior surfaces which are inert so that gas flowing through said apparatus from said sample port to said analytical column is only exposed to inert interior surfaces.

7. An apparatus according to claim 6, wherein said differential pressure switch, said expansion volume chamber, said primary collection trap, and said assist-/column interface have interior surfaces comprising a coating of fused silica so that gas flowing through said apparatus from said sample port to said analytical column is only exposed to surfaces of fused silica.

8. An apparatus according to claim 6, further comprising a secondary refocusing trap surrounding the analytical column.

9. An apparatus for connection to an analytical column of a gas chromatograph for analyzing samples for volatile organic compounds, comprising a differential pressure switch having a hollow interior and having:
 (a) a central helium port,
 (b) a sample flow port on a first side of said helium port, and
 (c) a sweep flow port on a second side of said helium port, wherein each of said ports extends from said hollow interior to outside said differential pressure switch
 (d) a vent end on a first end of said differential pressure switch, and
 (e) an assist/column flow end on an end of said differential pressure switch opposite said vent end; wherein said hollow interior of said differential pressure switch has an interior surface which is inert, wherein sample flow may be switched without mechanical means, and wherein the gas chromatograph and apparatus may be used with samples having anywhere from very high to very low levels of volatile organic compounds by changing timing and temperature parameters and by changing gas flow through the pressure switch nonmechanically, without changing anything else mechanically.

10. An apparatus according to claim 9, wherein said interior surface is made of fused silica so that gas flowing through said apparatus from said sample port to said analytical column is only exposed to surfaces of fused silica.

11. A chamber for use in gas chromatographic analysis after sample injection into a sample injector, and concentration of a sample on a primary collection trap, comprising:
 (a) an inlet tube, which is inserted into said sample injector;
 (b) a piece of tubing having a plurality of coils; and
 (c) an outlet tube, wherein said chamber allows heated inert transfer of the sample to the primary collection trap and thermal isolation of the primary collection trap from the sample injector, and wherein said chamber serves as a linear reservoir for the sample when condensed water, $CO_2$, or other major components of the sample expand rapidly.

12. A chamber according to claim 11, wherein said chamber further comprises an inert interior coating.

13. A chamber according to claim 12, wherein said coating comprises fused silica.

14. A primary collection trap comprising a piece of tubing coiled about a hollow rod, said rod comprising:
 (a) ports for a cryogenic substance to enter and exit said rod;
 (b) an inlet end;
 (c) a heater within said inlet end;
 (d) a tubing inlet end at said inlet end;
 (d) a tubing outlet which connects to an expansion volume tube connected to a gas chromatograph.

15. A primary collection trap according to claim 14, wherein said primary collection trap further comprises an inert interior coating.

16. A chamber according to claim 15, wherein said coating comprises fused silica.

* * * * *